United States Patent [19]

Cousse et al.

[11] Patent Number: 4,714,789
[45] Date of Patent: Dec. 22, 1987

[54] HALO-BIPHENYL TERTIARY ALCOHOLS USEFUL IN THERAPY IN THE TREATMENT OF ATHEROSCLEROSIS

[75] Inventors: Henri Cousse; André Delhon; Jean-Pierre Rieu; Jean-Francois Patoiseau, all of Castres, France

[73] Assignee: P. F. Medicament, Paris, France

[21] Appl. No.: 884,959

[22] Filed: Jul. 14, 1986

[30] Foreign Application Priority Data

Jul. 26, 1985 [FR] France .................. 85 11582

[51] Int. Cl.$^4$ ............................................. C07C 33/34
[52] U.S. Cl. ................................................. 568/807
[58] Field of Search ........................... 568/807; 436/71

[56] References Cited

U.S. PATENT DOCUMENTS 3,859,256  1/1975  Teufel et al. ................. 568/807
3,969,418  7/1976  Teufel et al. ................. 568/807

FOREIGN PATENT DOCUMENTS 2151311  4/1973  Fed. Rep. of Germany ...... 568/807
2341506  2/1975  Fed. Rep. of Germany ...... 568/807
 398522  3/1966  Switzerland ....................... 568/807

OTHER PUBLICATIONS

Inukia, "Chemical Abstracts", vol. 58, p. 66686 (1963).
Julia et al., "Chemical Abstracts", vol. 58, p. 6868 (1963).

Primary Examiner—Werren B. Lone
Attorney, Agent, or Firm—Gordon W. Hueschen

[57] ABSTRACT

The invention concerns halo-biphenyl tertiary alcohols of the general formula:

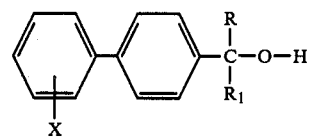

in which:
X is chlorine or bromine in ortho or meta position.
R and $R_1$, which may be identical or different, represent an alkyl group of low molecular weight having from 1 to 4 carbon atoms, inclusive.

These new derivatives are useful as medicaments, particularly in the treatment of atherosclerosis and obesity.

4 Claims, No Drawings

HALO-BIPHENYL TERTIARY ALCOHOLS USEFUL IN THERAPY IN THE TREATMENT OF ATHEROSCLEROSIS

The present invention relates to new derivatives of halo-biphenyl tertiary alcohols having lipid-reducing, cholesterol-reducing and anorectic properties, a method of preparing them, and their use as medicaments useful in the treatment and prevention and atherosclerotic disturbances and obesity.

In French Pat. Nos. 2,476,072 and 2,498,449 of the present applicant, there are set forth derivatives of halo-biphenyl carboxylic acids which can be used in the treatment of disturbances caused by atherosclerosis.

The new chemical compounds discovered by the applicant are of a new structure in view of the presence of the tertiary alcohol functional group.

The object of the present invention is halo-biphenyl tertiary alcohols of general formula (I):

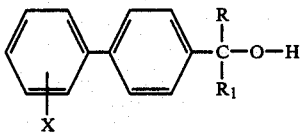

in which:
X represents a halogen atom and, more particularly, chlorine or bromine in ortho or meta position,
R and $R_1$, which are identical or different, represent an alkyl group of low molecular weight having 1 to 4 carbon atoms, inclusive, including butyl, isobutyl and t-butyl.

The present invention also concerns a method of preparing derivatives of formula I by reacting ketones of formula II:

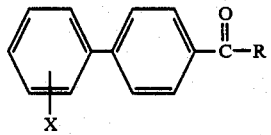

in which X has the same meaning as in formula I, with a magnesium derivative of the formula $R_1$—MgY (Y=iodine, bromine or chlorine) in accordance with the reaction mechanism:

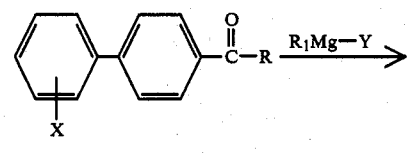

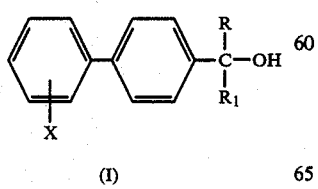

The present invention also concerns the use of the compounds of formula I as medicaments, as well as pharmaceutical compositions which contain these medicaments. The pharmaceutical compositions of the present invention may contain one or more compounds of formula I, possibly together with other active principles. Among the derivatives of formula I, the following may more particularly be mentioned:

(2'-chloro 4-biphenylyl)dimethyl carbinol (F 2833),
(2'-chloro 4-biphenylyl)ethyl methyl carbinol (F 2883),
(2'-chloro 4-biphenylyl)diethyl carbinol (F 2884),
(2'-chloro 4-biphenylyl)isopropylmethyl carbinol (F 2885),
(3'-chloro 4-biphenylyl)dimethyl carbinol (F 2886),
(2'-bromo 4-biphenylyl)dimethyl carbinol.

EXAMPLE 1

(2'-chloro 4-biphenylyl)dimethyl carbinol (F 2833)

A magnesium solution of methyl iodide is prepared from magnesium (2.53 g) and methyl iodide 7 ml (16.24 g, 0.114 mol) in ethyl ether (100 ml).

A solution of 2'-chloro 4-acetyl biphenyl (12 g, 52 mmol) in an ether/benzene mixture (60 ml:60 ml) is added, drop by drop, to said preparation.

After refluxing for one hour, the mixture is brought to room temperature and hydrolyzed by a saturated solution of ammonium chloride (20 ml, 0.09 mol).

The organic phase is removed and washed with water (100 ml), with bicarbonate (100 ml) and then with saline solution (100 ml).

After drying the solution over sodium carbonate, it is concentrated in vacuum at a temperature not greater than 40° C.

By extraction in heptane (100 ml) and cooling, the tertiary alcohol derivative is obtained in a yield of 80%.

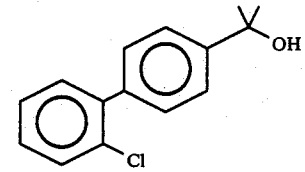

Empirical formula: $C_{15}H_{15}ClO$.
Molecular weight: 246.74.
Melting point: 55° C.
Thin-layer chromatography: support: silica gel 60 F 254 Merck; solvent: hexane/ethyl acetate; development: UV; Rf: 0.70.
Solubility: 1% in propylene glycol.

The following compounds were prepared in a manner similar to that described in Example 1, starting from suitable halogen derivatives and ketone.

EXAMPLE 2

(2'-chloro 4-biphenylyl)ethyl methyl carbinol (F 2883)
(obtained by using ethyl iodide)

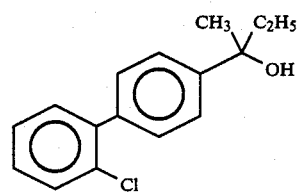

Empirical formula: $C_{16}H_{17}ClO$.
Molecular weight: 260.76.
Colorless oil: BP: 150° C. ($10^{-3}$ mbar); $n_D^{23}$: 1.5915.
Thin-layer chromatography: support: silica gel 60 F 254 Merck; solvent: hexane/ethyl acetate 70:30; development: UV; Rf: 0.5.
Solubility: 5% in propylene glycol.

EXAMPLE 3

(2'-chloro 4-biphenylyl)diethyl carbinol (F 2884) (obtained from 2'-chloro 4-propionyl biphenyl and ethyl iodide)

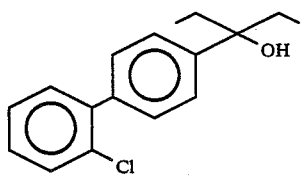

Empirical formula: $C_{17}H_{19}ClO$.
Molecular weight: 274.79.
Colorless oil: BP: 160° C. ($10^{-3}$ mbar); $n_D^{23}$: 1.5843.
Thin-layer chromatography: support: silica gel 60 F 254 Merck; solvent: hexane/ethyl acetate 70:30; development: UV; Rf: 0.60.
Solubility: 10% in propylene glycol.

EXAMPLE 4 (2'-chloro 4-biphenylyl)isopropylmethyl carbinol (F 2885) (obtained from 2'-chloro 4-acetyl biphenyl and isopropyl iodide)

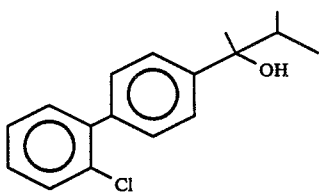

Empirical formula: $C_{17}H_{19}ClO$.
Molecular weight: 274.79.
Clear yellow oil: BP: 150° C. ($10^{-3}$ mbar); $n_D^{23}$: 1.5855.
Thin-layer chromatography: support: silica gel 60 F 254 Merck; solvent: hexane/ethyl acetate 70:30; development: UV; Rf: 0.60.
Solubility: 10% in propylene glycol.

EXAMPLE 5

(3'-chloro 4-biphenylyl)dimethyl carbinol (F 2886) (obtained from 3'-chloro 4-acetyl biphenyl and methyl iodide)

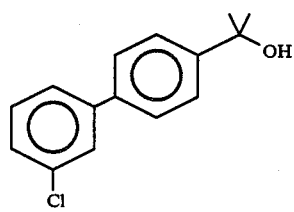

Empirical formula: $C_{15}H_{15}ClO$.
Molecular weight: 246.74.

Melting point: 71° C.
Thin-layer chromatography: support: silica gel 60 F 254 Merck; solvent: hexane/ethyl acetate 70:30; development: UV; Rf: 0.35.
Solubility: 2% in propylene glycol.

In similar manner there are obtained from the corresponding ketones:

EXAMPLE 6

(2'-bromo 4-biphenylyl)dimethyl carbinol

EXPERIMENTS

Various toxicological and pharmacological tests were carried out on the compounds forming the object of the present invention.

(A) Toxicology

The compounds of the invention were subjected to toxicological examinations. This toxicity was determined by the $LD_{50}$; it was determined on lots of 10 mice orally and intravenously and calculated in accordance with the method of MILLER and TAINTER (Proc. Soc. Exper. Biol. Med., 1944, 57, 261).

The $LD_{50}$ of the compounds tested is higher than 100 mg/kg intravenously and 1000 mg/kg orally.

(B) Pharmacological Properties

The pharmacological experiments made it possible to show remarkable lipid-reducing and cholesterol-reducing properties.

The results obtained with the products of Examples 1 to 5 are set forth below, compared with CLOFIBRATE and FENOFIBRATE.

Test covering 4 days of oral treatment by the method of BUCHMAN, SPRANCMANIS and PARTYKA (J. Med. Chem., 12, 1001-1006, 1969). Male rats, unprepared, Sprague Dawley, divided into homogeneous lots of 8 animals each.

Treatment orally with the products to be studied dissolved or suspended in 1% CMC in a volume of 10 mg/kg.

Duration of treatment: 4 days.
Frequency of treatments: Once a day.

On the fifth day, sampling of blood on heparin from the caudal artery after fasting for about 16 hours.

The results are set forth in the following table by way of comparison with CLOFIBRATE and FENOFIBRATE.

| Products | Dose mg/kg/day | Cholesterol, % decrease referred to control | Consumption of feed % variation referred to control |
|---|---|---|---|
| CLOFIBRATE | 100 | −17 | +14 |
|  | 200 | −8 (NS) | −10 |
|  | 300 | −12 (NS) | −40 |
| FENOFIBRATE | 100 | −16 | +23 |
|  | 200 | −27 | +10 |
|  | 300 | −25 | −17 |
| EXAMPLE 1 | 25 | −16 | −19 |
| (F 2833) | 50 | −31 | −20 |
|  | 100 | −39 | −30 |
| EXAMPLE 2 (F 2883) | 100 | −28 | 0 |
| EXAMPLE 3 (F 2884) |  | −41 | 0 |
| EXAMPLE 4 (F 2885) |  | −10 | 0 |
| EXAMPLE 5 (F 2886) |  | 0 | −40 |

(C) Therapeutic Applications

Based on their pharmacological properties, the compounds of the invention, and more especially the compounds of Examples 1, 2, 3 and 4, can be used in therapy in the treatment of the various types of hyperlipidemias for the prevention and treatment of artherosclerosis and obesity. The pharmaceutical preparations containing these active principles can be administered orally or parenterally. It is also possible to combine with them other pharmaceutically and therapeutically acceptable active principles.

On a basis of their pharmacological properties and their low toxicity, the compounds of the invention can be employed for lipid-lowering and cholesterol-lowering in a subject in need of the same, as well as for their anorexigenic effect in a subject in need of the same, and accordingly may be employed in the form of pharmaceutical preparations which facilitate bioavailability and/or in the form of pharmaceutical compositions thereof containing an effective amount of the active ingredient together with a pharmaceutically-acceptable carrier, diluent, or adjuvant. The preparations may as usual be provided in solid form, for example, in form of tablets, pills, capsules, or the like, or liquid form, for example, in the form of solutions, suspensions, or emulsions. Alternatively, the pharmaceutical preparations may be made available in a form suitable for injection by subjecting the same to conventional pharmaceutical operations such as sterilization, and in any event may contain adjuvants, for instance, preservatives, stabilizers, wetting or emulsifying agents, buffers, and the usual carriers or inert pharmaceutically-acceptable diluents such as sugar, starch, water, or the like. The doses in which the active compounds and the pharmaceutical compositions thereof may be administered vary widely depending upon the subject, but daily doses of from about 0.1 g to 1 mg/kg of body weight and which approximate or are somewhat lower than those usual for Clofibrate and/or Fenofibrate may be employed. The pharmaceutical compositions of the invention can be used in human or veterinary medicine where indicated, for instance, in the cholesterol-reduction and lipid-reduction of a subject in need of the same, as well as for their anorexigenic effect in the reduction of diet or the treatment of obesity. Other active principles may of course be associated with the compounds of the invention, in order to supplement or reinforce their therapeutic activity within a given pharmaceutical composition or for a given pharmaceutical indication, as is conventional in the art.

In conclusion, from the foregoing, it is apparent that the present invention provides novel compounds which are useful for their lipid- and cholesterol-reducing properties, a process for the production thereof, pharmaceutical compositions comprising the same, and a method of treating a subject in need of such lipid-reduction and/or cholesterol-reduction by treating the said subject with a lipid-reducing and cholesterol-reducing amount of a compound of the invention, all of the foregoing compounds, process, compositions, and method of treating having the foregoing enumerated characteristics and advantages.

It is to be understood that the invention is not to be limited to the exact details of operation or to the exact compositions, methods, procedures, or embodiments shown and described, as obvious modifications and equivalents will be apparent to one skilled in the art, and the invention is therefore to be limited only by the full scope of the appended claims.

We claim:

1. Halo-biphenyl tertiary alcohols of general formula (I):

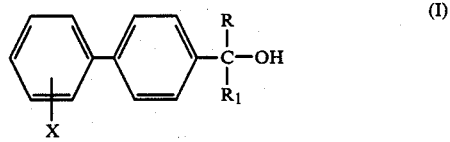

in which:
X represents a chlorine or bromine atom in ortho or meta position,
R and $R_1$ are identical or different and represent an alkyl group of low molecular weight having 1 to 4 carbon atoms, inclusive.

2. A compound according to claim 1, characterized by the fact that it is selected from among:
(2'-chloro 4-biphenylyl)dimethyl carbinol (F 2833),
(2'-chloro 4-biphenylyl)ethyl methyl carbinol (F 2883),
(2'-chloro 4-biphenylyl)diethyl carbinol (F 2884),
(2'-chloro 4-biphenylyl)isopropylmethyl carbinol (F 2885),
(3'-chloro 4-biphenylyl)dimethyl carbinol (F 2886),
(2'-bromo 4-biphenylyl)dimethyl carbinol.

3. A method of lipid reduction and cholesterol reduction in a subject in need thereof which comprises the step of orally or parenterally administering to the said subject a lipid-reducing and cholesterol-reducing amount of a compound of claim 1.

4. A pharmaceutical composition suitable for oral or parenteal use in lipid- and cholesterol-reduction in a subject in need thereof which comprises a lipid- and cholesterol-reducing amount of a compound of claim 1 together with a pharmaceutically-acceptable carrier or diluent.

* * * * *

UNITED STATES PATENT AND TRADEMARK OFFICE
CERTIFICATE OF CORRECTION

PATENT NO.  : 4,714,789

DATED       : December 22, 1987

INVENTOR(S) : Henri Cousse, André Delhon, Jean-Pierre Rieu and Jean-Francois Patoiseau It is certified that error appears in the above-identified patent and that said Letters Patent is hereby corrected as shown below:

Title Page, [56] References Cited, OTHER PUBLICATIONS (second column), line 1; "p. 66686" should read -- p. 6668b --

Col. 3, line 30; "EXAMPLE 4" should be a heading by itself (it should be moved up one line)
Col. 4, line 39; "mg/kg." should read -- ml/kg. --
Col. 6, line 49; "parenteal" should read -- parenteral --

Signed and Sealed this

Fourteenth Day of June, 1988

Attest:

DONALD J. QUIGG

*Attesting Officer*        *Commissioner of Patents and Trademarks*